United States Patent
Thum et al.

(10) Patent No.: US 11,208,651 B2
(45) Date of Patent: Dec. 28, 2021

(54) COMPOUND FOR TREATMENT OF HEART FAILURE

(71) Applicant: Medizinische Hochschule Hannover, Hannover (DE)

(72) Inventors: Thomas Thum, Hannover (DE); Sandor Batkai, Hannover (DE); Ariana Foinquinos, Amsterdam (NL)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 16/769,873

(22) PCT Filed: Dec. 14, 2018

(86) PCT No.: PCT/EP2018/085008
§ 371 (c)(1),
(2) Date: Jun. 4, 2020

(87) PCT Pub. No.: WO2019/115788
PCT Pub. Date: Jun. 20, 2019

(65) Prior Publication Data
US 2021/0180054 A1    Jun. 17, 2021

Related U.S. Application Data

(60) Provisional application No. 62/599,050, filed on Dec. 15, 2017.

(30) Foreign Application Priority Data

Dec. 15, 2017 (EP) .................................... 17207738

(51) Int. Cl.
*C12N 15/11* (2006.01)
*A61P 19/04* (2006.01)
*A61P 9/04* (2006.01)
*A61K 45/06* (2006.01)
*C07H 21/04* (2006.01)

(52) U.S. Cl.
CPC ............. *C12N 15/11* (2013.01); *A61K 45/06* (2013.01); *A61P 9/04* (2018.01); *A61P 19/04* (2018.01); *C07H 21/04* (2013.01); *C12N 2310/315* (2013.01); *C12N 2310/3231* (2013.01); *C12N 2310/351* (2013.01); *C12N 2320/31* (2013.01)

(58) Field of Classification Search
None
See application file for complete search history.

(56) References Cited

U.S. PATENT DOCUMENTS 6,867,184 B2    3/2005    Treadway

FOREIGN PATENT DOCUMENTS

| EP | 2474617 A1 | 7/2012 |
|---|---|---|
| WO | 2010/105096 A2 | 9/2010 |
| WO | 2013/034653 A1 | 3/2013 |
| WO | 2016/042561 A2 | 3/2016 |

OTHER PUBLICATIONS

Extended European Search Report for EP Application No. 17207738.0 dated May 17, 2018 (11 pages).
Barry et al., "What Causes a Broken Heart—Molecular Insights into Heart Failure," Int'l Review of Cell and Molecular Biology, 2010, 284:113-179.
Datta et al., "Cellular Survival: A Play in Three Akts," Genes & Development, 1999, 13:2905-2927.
Debosch et al., "Insulin Signaling Pathways and Cardiac Growth," J Mol Cell Cardiol., 2008, 44(5):855-864.
Frescas et al., "Nuclear Trapping of the Forkhead Transcription Factor FoxO1 via Sirt-Dependent Deacetylation Promotes Expression of Glucogenetic Genes," The Journal of Biological Chemistry, 2005, 290(21):20589-20595.
Glass, "PI3 Kinase Regulation of Skeletal Muscle Hypertrophy and Atrophy," Current Topics in Microbiology and Immunology, 2010, 346:267-278.
Gottlieb et al., "Mitochondrial Turnover in the Heart," Biochim Biophys Acta., 2011, 1813(7):1295-1301.
Hannin, "Supplemenary material "miRNA-132 induces hepatic steatosis and hyperlipidaemia by synergistic multitarget suppression"", 2017, XP55471789.
Hill et al., "Cardiac Plasticity," N Engl J Med, 2008, 358:1370-1380.
Hinkel et al., "P5384 LNA-based miRNA132 Inhibition is Cardioprotective in a Pig Model of Percutaneous Transverse Aortic Constriction (pTAC)," European Heart Journal, 2017, 38:1139.
Kolk et al., "LAD-Ligation: A Murine Model of Myocardial Infarction," Journal of Visualized Experiments, 2009, 3 pages.
McMullen et al., "The Insulin-Like Growth Factor 1 Receptor Induces Physiological Heart Growth via the Phosphoinositide 3-Kinase (P110α) Pathway," The Journal of Biological Chemistry, 2004, 279(6):4782-4793.
Ni et al., "Foxo Transcription Factors Blunt Cardiac Hypertrophy by Inhibiting Calcineurin Signaling," Circulation, 2006, 114(11):1159-1168.
Ronnebaum et al., "The FoxO Family in Cardiac Function and Dysfunction," Annu Rev Physiol., 2010, 72:81-94.
Skurk et al., "The FOXO3a Transcription Factor Regulates Cardiac Myocyte Size Downstream of AKT Signaling," J Biol Chem., 2005, 280(21):20814-20823.
PCT International Search Report and Written Opinion for PCT Application No. PCT/EP2018/085008 dated Mar. 21, 2019 (13 pages).

(Continued)

*Primary Examiner* — Ekaterina Poliakova-Georgantas
(74) *Attorney, Agent, or Firm* — Eversheds Sutherland (US) LLP

(57) ABSTRACT

The present invention refers to an oligonucleotide which is an effective inhibitor of microRNA miR-132 and its use in medicine, particularly in the prevention or treatment of cardiac and/or fibrotic disorders.

28 Claims, 20 Drawing Sheets

Specification includes a Sequence Listing.

(56) References Cited

OTHER PUBLICATIONS

Alzahrani et al., "Enhancing miR-132 Expression by Aryl Hydrocarbon Receptor Attenuates Tumorigenesis Associated with Chronic Colitis," International Immunopharmacology, 2017, 52:342-351.
Fiedler et al., "Hormonal Regulation of MicroRNA Expression in Periovulatory Mouse Mural Granulosa Cells," Biology of Reproduction, 2008, 79:1030-1037.
Hanin et al., "miRNA-132 Induces Hepatic Steatosis and Hyperlipidaemia by Synergistic Multitarget Suppression," Gut, 2018, 67:1124-1134.
Hou et al., "Positive Feedback Regulation Between microRNA-132 and CREB in Spinal Cord Contributes to Bone Cancer Pain in Mice," Eur. J. Pain, 2016, 20:1299-1308.
Jimenez-Mateos et al., "miRNA Expression Profile after Status Epilepticus and Hippocampal Neuroprotection by Targeting miR-132," The American Journal of Pathololgy, 2011, 179(5):2519-2532.
Leinders et al., "Increased miR-132-3p Expression in Associated with Chronic Neuropathic Pain," Exp. Neurol, 2016, 283(Pt A):276-286.
Shaked et al., "MicroRNA-132 Potentiates Cholinergic Anti-Inflammatory Signaling by Targeting Acetylcholinesterase," Immunity, 2009, 31:965-973.
Ucar et al., "The miRNA-212/132 Family Regulates Both Cardiac Hypertrophy and Cardiomyocyte Autophagy," Nature Communications, 2012, 11 pages.
International Preliminary Report on Patentability for PCT/EP2018/085008 dated Mar. 4, 2020 (20 pages).

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: inhibitor
<220> FEATURE:
<221> NAME/KEY: misc_feature
<222> LOCATION: (1)..(16)
<223> OTHER INFORMATION: at least one G or T is a bridged and/or a
      morpholino building block

<400> SEQUENCE: 1
atggctgtag actgtt                                                        16

<210> SEQ ID NO 2
<211> LENGTH: 16
<212> TYPE: DNA
<213> ORGANISM: Artificial Sequence
```

-continued

```
<220> FEATURE:
<223> OTHER INFORMATION: inhibitor
<220> FEATURE:
<221> NAME/KEY: misc_feature
<222> LOCATION: (2)..(2)
<223> OTHER INFORMATION: bridged or morpholino building block
<220> FEATURE:
<221> NAME/KEY: misc_feature
<222> LOCATION: (4)..(4)
<223> OTHER INFORMATION: bridged or morpholino building block
<220> FEATURE:
<221> NAME/KEY: misc_feature
<222> LOCATION: (6)..(6)
<223> OTHER INFORMATION: bridged or morpholino building block
<220> FEATURE:
<221> NAME/KEY: misc_feature
<222> LOCATION: (8)..(8)
<223> OTHER INFORMATION: bridged or morpholino building block
<220> FEATURE:
<221> NAME/KEY: misc_feature
<222> LOCATION: (10)..(10)
<223> OTHER INFORMATION: bridged or morpholino building block
<220> FEATURE:
<221> NAME/KEY: misc_feature
<222> LOCATION: (15)..(15)
<223> OTHER INFORMATION: bridged or morpholino building block
<220> FEATURE:
<221> NAME/KEY: misc_feature
<222> LOCATION: (16)..(16)
<223> OTHER INFORMATION: bridged or morpholino building block

<400> SEQUENCE: 2
atggctgtag actgtt                                                    16

<210> SEQ ID NO 3
<211> LENGTH: 16
<212> TYPE: DNA
<213> ORGANISM: Artificial Sequence
<220> FEATURE:
<223> OTHER INFORMATION: CDR132L
<220> FEATURE:
<221> NAME/KEY: misc_feature
<222> LOCATION: (1)..(1)
<223> OTHER INFORMATION: 2'deoxyadenosine
<220> FEATURE:
<221> NAME/KEY: misc_feature
<222> LOCATION: (1)..(15)
<223> OTHER INFORMATION: phosphorothioate linkage
<220> FEATURE:
<221> NAME/KEY: misc_feature
<222> LOCATION: (2)..(2)
<223> OTHER INFORMATION: LNA building block
<220> FEATURE:
<221> NAME/KEY: misc_feature
<222> LOCATION: (3)..(3)
<223> OTHER INFORMATION: 2'deoxyguanosine
<220> FEATURE:
<221> NAME/KEY: misc_feature
<222> LOCATION: (4)..(4)
<223> OTHER INFORMATION: LNA building block
<220> FEATURE:
<221> NAME/KEY: misc_feature
<222> LOCATION: (5)..(5)
<223> OTHER INFORMATION: 2'deoxycytidine
<220> FEATURE:
<221> NAME/KEY: misc_feature
<222> LOCATION: (6)..(6)
<223> OTHER INFORMATION: LNA building block
<220> FEATURE:
<221> NAME/KEY: misc_feature
<222> LOCATION: (7)..(7)
<223> OTHER INFORMATION: 2'deoxyguanosine
<220> FEATURE:
<221> NAME/KEY: misc_feature
<222> LOCATION: (8)..(8)
<223> OTHER INFORMATION: LNA building block
<220> FEATURE:
```

```
<221> NAME/KEY: misc_feature
<222> LOCATION: (9)..(9)
<223> OTHER INFORMATION: 2'deoxyadenosine
<220> FEATURE:
<221> NAME/KEY: misc_feature
<222> LOCATION: (10)..(10)
<223> OTHER INFORMATION: LNA building block
<220> FEATURE:
<221> NAME/KEY: misc_feature
<222> LOCATION: (11)..(11)
<223> OTHER INFORMATION: 2'deoxyadenosine
<220> FEATURE:
<221> NAME/KEY: misc_feature
<222> LOCATION: (12)..(12)
<223> OTHER INFORMATION: 2'deoxycytidine
<220> FEATURE:
<221> NAME/KEY: misc_feature
<222> LOCATION: (13)..(13)
<223> OTHER INFORMATION: thymidine
<220> FEATURE:
<221> NAME/KEY: misc_feature
<222> LOCATION: (14)..(14)
<223> OTHER INFORMATION: 2'deoxyguanosine
<220> FEATURE:
<221> NAME/KEY: misc_feature
<222> LOCATION: (15)..(16)
<223> OTHER INFORMATION: LNA building block

<400> SEQUENCE: 3
atggctgtag actgtt                                                       16
```

COMPOUND FOR TREATMENT OF HEART FAILURE

CROSS REFERENCE TO RELATED APPLICATIONS

This application claims the priority benefit of PCT/EP2018/085008 filed on Dec. 14, 2018 which claims priority benefit of U.S. Provisional Application No. 62/599,050, filed Dec. 15, 2017 and European Patent Application No. 17207738.0, filed Dec. 15, 2017. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 7, 2020, is named SequenceListing.txt and is 65,536 bytes in size.

The present invention refers to an oligonucleotide which is an effective inhibitor of the microRNA miR-132, and its use in medicine, particularly in the prevention or treatment of cardiac disorders and/or fibrotic disorders.

Heart failure is one of the leading pathological causes of mortality in the world. Myocardial infarction (MI) is the most important cause of heart failure as MI leads to subsequent progressive remodeling of the heart resulting in heart failure with poor prognosis. The currently used therapeutic pharmacologic options for heart failure include angiotensin-modulating agents, β-blockers, diuretics, aldosterone antagonists, combined neprilysin-inhibitor with angiotensin-II-receptor blocker, vasodilators, or inotropic agents. Although several clinical studies have shown significant decreases in heart failure-induced mortality rates for all these agents, the 5-year mortality rate remains unacceptably at almost 50%. Thus, there is a great need to develop novel and more efficient therapeutic approaches for heart failure.

Pathological hypertrophic growth of cardiomyocytes can lead to the development of cardiac remodeling, heart failure and sudden cardiac death. Hypertrophic growth of cardiomyocytes is a response to increased cardiac wall stress caused by cardiac volume and/or pressure overload. Initially, cardiac hypertrophy is a compensatory mechanism aiming to decrease wall stress and to increase cardiac output. However, prolonged cardiac hypertrophy progresses to contractile dysfunction, cardiac decompensation and finally heart failure (Hill and Olson, 2008; Barry and Townsend, 2010). The transition from physiological to pathological hypertrophy can occur depending on many factors including myocyte loss through apoptosis or necrosis, alterations in autophagy, defects in contractile response, dysregulated calcium homeostasis, desensitization of adrenergic receptors, or cardiac fibrosis (Hill and Olson, 2008; Barry and Townsend, 2010). Hypertrophic signaling is largely mediated by the insulin signaling pathway (DeBosch and Muslin, 2008; Barry and Townsend, 2010). Both insulin and insulin-like growth factor-1 (IGF-1) activate pro-hypertrophic pathways in cardiomyocytes via the IGF-1 receptor, which activates the phosphoinositine-3-kinase (PI3K) (McMullen et al., 2004). PI3K activity leads to the activation of the serine/threonine kinase Akt via its phosphorylation and active Akt phosphorylates anti-hypertrophic FoxO transcription factors leading to their de-stabilization and prevention of nuclear localization (Datta et al., 1999; Skurk et al., 2005; Ronnebaum and Patterson, 2010). In contrast, acetylation of FoxO factors by sirtuin-1 (Sirt-1) leads to their stabilization and nuclear translocation (Frescas et al., 2005). Stabilized FoxO transcription factors are localized in the nucleus in order to regulate the expression of anti-hypertrophic genes. The anti-hypertrophic functions of FoxO proteins are largely mediated through suppression of the pro-hypertrophic calcineurin signaling pathway via the expression of anti-hypertrophic gene targets of FoxO factors, such as atrogin-1 (Ni et al., 2006; Ronnebaum and Patterson, 2010; Glas, 2010). Moreover, FoxO transcription factors also induce apoptosis and regulate autophagy in cardiomyocytes (Ronnebaum and Patterson, 2010).

MicroRNAs have been shown to have a key role in adverse cardiac remodeling. WO 2013/034653 describes that miR-132 and/or miR-212 may induce cardiac hypertrophy and thus constitute potential therapeutic targets for heart failure treatment.

WO 2016/042561 describes a method of treating a lipid-related disorder by administering to the subject a therapeutically effective amount of a polynucleotide agent which is substantially complementary to a nucleotide sequence of a human miR-132.

Figure 1A:
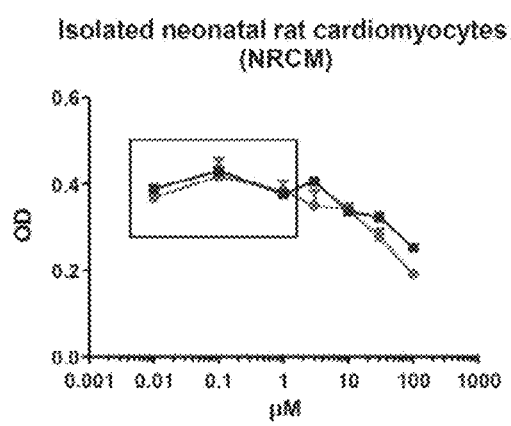
FIG. 1A: Effect of CDR132L compared to a scrambled LNA oligonucleotide, used as control in isolated neonatal cardiomyocytes (NRCM).

The present inventors have identified a novel oligonucleotide analogue which is an effective inhibitor of miR-132 expression in cardiomyocytes. The oligonucleotide analogue, in the following designated CDR132L, is a mixmer consisting of DNA and LNA building blocks, having internucleosidic phosphorothioate linkages. It lacks significant toxicity in a human liver cell line and isolated neonatal rat cardiomyocytes. Further, it was shown that CDR132L exhibits superior effects compared to other oligonucleotide analogues having the same nucleotide sequence but a different distribution of LNA building blocks.

The efficacy of CDR132L was tested in several animal models. In a transgenic mouse model of cardiac hypertrophy, CDR132L led to reverse cardiac remodeling associated with reduced expression of miR-132. In a mouse model of post-MI heart failure it was found that CDR132L treatment reduces post-MI left ventricular dysfunction and load independent parameters of systolic contractile function. Further, administration of CDR132L resulted in an improvement of cardiac function, and reduces miR-132 expression, cardiac stress signaling and post-MI hypertrophy. In a pig model of post-MI heart failure CDR132L treatment was found to avert maladaptive remodeling and to improve left ventricular function. Further, CDR132L normalizes the tissue expression of pathologic heart failure markers such as BNP, ANP and provides a shift in myosine heavy change isoforms (MYH7/6 ratio).

In an additional study, the present inventors have identified antifibrotic therapeutic effects for the oligonucleotide analogue CDR132L in an in vivo mouse model of myocardial infarction and in vitro models of liver fibrosis and lung fibrosis.

Thus, the oligonucleotide CDR132L is useful as an active agent in medicine, particularly in the prevention or treatment of cardiac disorders and/or fibrotic disorders.

Accordingly, a first aspect of the present invention provides an oligonucleotide analogue, comprising a sequence of formula I:

5'-ATGGCTGTAGACTGTT-3' (SEQ ID NO: 1)

wherein A, T, G and C are deoxyribonucleotide building blocks and wherein at least one G or T building block is a bridged nucleotide building block, and/or a morpholino nucleotide building block.

In a particular embodiment, the oligonucleotide comprises or has the sequence of formula II:

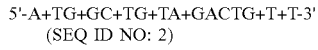

5'-A+TG+GC+TG+TA+GACTG+T+T-3'
(SEQ ID NO: 2)

wherein A, T, G and C are deoxyribonucleotide building blocks and wherein +G and +T are bridged nucleotide building blocks and/or morpholino nucleotide building blocks, particularly wherein +G and +T are LNA building blocks.

The oligonucleotide analogue of formula I or formula II may comprise at least one modified internucleosidic linkage, e.g. an internucleosidic linkage which is stabilized against nuclease digestion, e.g. a phosphorothioate or a phosphorodiamidate linkage. In specific embodiments, all internucleosidic linkages are modified linkages, particularly phosphorothioate linkages.

In a more specific embodiment, the invention relates to the oligonucleotide CDR132L as described herein.

The oligonucleotide CDR132L has a sequence of formula III:

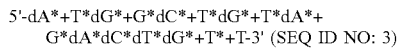

5'-dA*+T*dG*+G*dC*+T*dG*+T*dA*+
G*dA*dC*dT*dG*+T*+T-3' (SEQ ID NO: 3)

wherein dA is 2'deoxyadenosine, dG is 2'deoxyguanosine, dC is 2'deoxycytidine and T is thymidine,
wherein +T is an LNA-T building block and +G is an LNA-G building block and wherein * is a phosphorothioate linkage.

A further aspect of the present invention relates to a pharmaceutical composition comprising as an active agent an oligonucleotide analogue comprising a sequence of formula I, II or III and a pharmaceutically acceptable carrier.

Still a further aspect of the present invention relates to the medical use of an oligonucleotide analogue comprising a sequence of formula I, II or III. In certain embodiments, the medical use relates to a use for the treatment or prevention of a disorder associated with, accompanied by and/or caused by pathological expression of miR-132. In certain embodiments, the medical use relates to the treatment or prevention of cardiac disorders, particularly cardiac hypertrophy-associated disorders. In certain embodiments, the medical use relates to the treatment of fibrotic disorders, e.g. disorders associated with, accompanied by and/or caused by pathological fibrosis, particularly cardiac fibrotic disorders, pulmonary fibrotic disorders or hepatic fibrotic disorders.

The oligonucleotide of formula I, II or III may consist of deoxyribonucleotide DNA building blocks and bridged nucleotide building blocks and/or morpholino nucleotide building blocks (DNA). A "bridged nucleotide" refers to a modified ribonucleotide wherein the ribose moiety comprises a two-or-three atom bridge connecting the 2'- and the 4'-carbon atom. For example, the bridge may comprise the structure 2'-O—CH$_2$-4', 2'-O—CH$_2$—CH$_2$-4', 2'-O—CH (CH$_3$)-4' or a corresponding structure where O is replaced by S or NH. In a particular embodiment, the at least one bridged nucleotide building block is a locked nucleic acid (LNA) building block having a 2'-O—CH$_2$-4'-bridge. A morpholino nucleotide building block refers to a modified nucleotide wherein the ribose or deoxyribose is replaced by a morpholino moiety.

The oligonucleotide of formula I, II or III has a length of at least 16 building blocks, e.g. a length of 16 to 20 building blocks. In a particular embodiment, the oligonucleotide of formula I, II or III has a length of 16 building blocks.

In some embodiments, the oligonucleotide of formula I, II or III comprises 5 to 10, e.g. 6 to 8, particularly, 7 bridged nucleotide building blocks, e.g. LNA building blocks and/or morpholino nucleotide building blocks.

In some embodiments, the oligonucleotide of formula I, II or III is a naked oligonucleotide. In some embodiments, the oligonucleotide may be conjugated to at least one heterologous moiety, e.g. a moiety which does not contribute to the binding of the oligonucleotide to miR-132. The heterologous moiety may be a moiety which improves targeting and/or cellular uptake, e.g. a lipid moiety such as cholesterol or a fatty acid, a saccharide or amino saccharide moiety such as a N-galactosamine containing moiety, a peptide or polypeptide moiety or a nucleosidic or nucleotidic moiety such as an aptamer. A heterologous moiety may be conjugated with the 5'- and/or 3'-terminus of the oligonucleotide analogue by means of covalent bond or a spacer.

The oligonucleotide of the present invention is suitable for use in medicine including human and veterinary medicine. In certain embodiments, the compound is useful in the prevention or treatment of a disorder associated with, accompanied by and/or caused by pathological expression, e.g. overexpression of miR-132. Administration of the compound was found to significantly reduce miR-132 expression in vitro and in vivo.

In some embodiments, the compound may be administered to patients showing an overexpression of miR-132 compared to healthy subjects. In some embodiments, the compound may be administered to patients not showing an overexpression of miR-132 compared to healthy subjects but still in need of a reduction of the level of miR-132.

The term "prevention" in the context of the present invention relates to the administration of the compound to a patient who is known to have an increased risk of developing a certain disorder. The term "treatment" in the context of the present invention relates to the administration of the compound to a patient which has already developed signs and/or symptoms of a certain disorder. The term "patient" relates to a subject in need of administration of the compound of the invention in the field of human or veterinary medicine. In specific embodiments the patient is a human patient.

In certain embodiments, the compound of the present invention is useful in the prevention or treatment of cardiac disorders, particularly of cardiac hypertrophy-associated disorders. For example, the compound is useful in the prevention or treatment of contractile dysfunction, cardiac decompensation, heart failure or for the prevention or treatment of cardiac remodeling after myocardial infarction, myocarditis, valvular heart diseases such as aortic stenosis or mitral valve insufficiency, genetic cardiac disorders with cardiac hypertrophy, e.g. hypertrophic non-obstructive and obstructive cardiomyopathy or Fabry disease.

The compound is useful for administration to patients selected from
 (i) patients having an increased risk for developing heart failure,
 (ii) patients suffering from (congestive) heart failure, e.g. patients having an increased risk of heart failure progression,
 (iii) post-myocardial infarction patients and/or
 (iv) patients with congenital heart diseases associated with cardiac hypertrophy, such as pulmonal vein stenosis, atrial or ventricular septum defects.

In certain embodiments, the compound of the present invention is useful in the prevention or treatment of fibroctic disorders, particularly disorders associated with, accompanied by and/or caused by pathological fibrosis.

Pathological fibrosis is the formation of excess fibrous connective tissue in an organ or tissue, particularly associated with, accompanied by and/or caused by a pathological state. Pathological fibrosis can occur in many different organs and tissues within the body, typically as a result of inflammation or damage.

In a certain embodiment, the fibrosis is a cardiac fibrosis, e.g. a condition involving pathological fibrosis in the heart. Exemplary types of cardiac fibrosis include atrial fibrosis, endomyocardial fibrosis or fibrosis resulting from a previous myocardial infarction.

In a further embodiment, the fibrosis is a pulmonary fibrosis, e.g. a condition involving pathological fibrosis in the lung. Exemplary types of pulmonary fibrosis include fibrotic disorders caused by occupational or environmental factors, for example by exposure to toxins and pollutants such as silica dust, asbestos fibers, metal dust, coal dust, grain dust, bird and animal droppings. Other types of pulmonary fibrotic disorders are caused by radiation treatment and/or treatment with medicaments such as chemotherapeutic drugs, cardiac drugs, antibiotics or anti-inflammatory drugs. Still other types of pulmonary fibrotic disorders are caused by disorders including idiopathic pulmonary fibrosis, dermatitis, polymyositis, mixed connective tissue disease, an autoimmune disease such as rheumatoid arthritis, scleroderma, Sjogren's syndrome or systemic lupus erythematosus, sarcoidosis, pneumonia, a viral infection or gastroesophageal reflux disease (GERD).

In a further embodiment, the fibrosis may be hepatic fibrosis, e.g. a conditions involving pathological fibrosis in the liver. Exemplary types of hepatic fibrosis are caused by a viral infection, e.g. by hepatitis B and/or C virus, hereditary metabolic disorders, autoimmune hepatitis, biliary obstruction, iron overload, non-alcoholic fatty liver disease, including non-alcoholic fatty liver (NAFL) and non-alcoholic steatohepatitis (NASH) and alcohol liver disease.

In still further embodiments, the fibrosis may also be a vascular fibrosis, e.g. arterial stiffness, a cutaneous fibrosis, e.g. keloid formation or nephrogenic systemic fibrosis, an arthrofibrosis, some forms of adhesive capsulitis, soft tissue fibrosis such as mediastinal fibrosis or retroperitoneal fibrosis or bone marrow fibrosis such as myelofibrosis.

In certain embodiments, the invention encompasses determining the amount and/or activity of certain physiological parameters in the subject to be treated before, during and/or after administration of the compound of the invention. This concomitant diagnostic procedure may provide assistance for the medical use as described above. For example, the diagnostic procedure may provide assistance in risk assessment, patient stratification, monitoring of treatment course and/or post-treatment control.

In certain embodiments, the invention encompasses determining the amount and/or activity of miR-132 in the subject to be treated before, during and/or after administration of the compounds of the invention. In further embodiments, the invention encompasses determining the amount and/or activity of cardiac markers such as BNP, ANP or myosine heavy change isoforms, e.g. the MYH7/6 ratio, and/or the levels of FoxO3 and/or SERCA2. In still further embodiments, the invention encompasses determining the amount and/or activity of fibrotic markers such as collagen, e.g. collagen deposition and/or expression of fibrotic marker genes such as collagen 1A1, collagen 1A2, collagen 3A1 and/or a matrix metallopeptidase such as matrix metallopeptidase 2.

The determination of the above parameters may be carried out in body fluid samples such as blood, plasma or serum or in tissue samples according to known methods at the nucleic acid and/or protein level and may provide useful diagnostic information, e.g. on the course and/or success of the treatment.

The compound of the invention may be administered as a pharmaceutical composition comprising a pharmacologically acceptable carrier. Administration may be carried out by known methods, wherein the compound is introduced into the desired target cell or organ of the subject to be treated.

The compound may be administered as such or as a conjugate with a heterologous moiety as described above.

For pharmaceutical applications, the composition may be in the form of a solution, e.g. an injectable solution, emulsion, inhalation, suspension or the like.

The composition may be administered in any suitable way, e.g. parenterally, in particular by injection such as subcutaneous, intramuscular, intravenous or intraarterial injection, or, infusion, by oral or inhalative intake and/or by dermal application. The carrier may be any suitable pharmaceutical carrier. Preferably, a carrier is used which is capable of increasing the efficacy of oligonucleotide molecules to enter the target cells. Suitable examples of such carriers are liposomes, e.g. cationic liposomes, or predesigned exosomes.

The compound is administered in a pharmaceutically effective dosage depending on the route of administration and the type or severity of the disease.

The compound may be administered as a monotherapy or in combination with a further different medicament, particularly a medicament suitable for the prevention or treatment of cardiac disorders or fibrotic disorders as described above.

Examples of further medicaments suitable for the prevention or treatment of cardiac disorders are angiotensin-modulating agents, β-blockers, diuretics, aldosterone antagonists, vasodilators, ionotrophic agents, statins, or neprilysin-inhibitors or combinations thereof, e.g. a combination of a neprilysin-inhibitor, e.g. sacubitril, with an angiotensin-II-receptor blocker, e.g. valsartan.

Examples of further medicaments suitable for the prevention of treatment of fibrotic disorders are medicaments for the prevention or treatment of cardiac fibrosis such as ACE inhibitors, e.g. lisinopril, Angiotensin II receptor blockers, e.g. candesartan, losartan or olmesartan, aldosteron antagonists, e.g. spironolactone and/or TGF β inhibitors, e.g. pirfenidone or tranilast, medicaments for the prevention or treatment of pulmonary fibrosis such as anti-fibrotic agents, e.g. nintedanib or pirfenidone, anti-inflammatory agents, e.g. corticosteroids, azathioprine, cyclophosphamide and mycophenolate mofetil, anti-reflux agents, e.g. protein pump inhibitors or $H_2$ blockers and/or anti-coughing agents and medicaments for the prevention and/or treatment of hepatic fibrosis such as ACE inhibitors, e.g. benazepril, lisinopril or ramipril, antiviral agents or PPAR α-agonists.

Still further, the invention relates to the use of a compound of the invention as described herein above for the manufacture of a medicament for the prevention or treatment of a cardiac disorder.

Still further, the invention relates to the use of a compound of the invention as described herein above for the manufacture of a medicament for the prevention or treatment of a fibrotic disorder.

Still further, the invention relates to a method for the prevention or treatment of a cardiac disorder comprising administering to a subject in need thereof a therapeutically effective amount of at least one compound as described herein.

Still further, the invention relates to a method for the prevention or treatment of a fibrotic disorder comprising administering to a subject in need thereof a therapeutically effective amount of at least one compound as described herein.

Further, the present invention shall be described in more detail by the following Figures and Examples.

EXAMPLE 1—SILENCING OF MIR-132 EXPRESSION IN CARDIOMYOCYTES

A quantitative in vitro assay for miRNA inhibitory activity of numerous structure analogue compounds derived form an anti-miR-132 library was carried out. Silencing of miRNA expression was quantified by a TaqMan® assays and quantitative real-time PCR.

The study was conducted in isolated rat cardiomyocytes after hypertrophic stimulation by phenylephrine/isoproterenol treatment in concentrations of 10 μM. Cells were incubated for 48 hours in standard cell culture medium. Test compounds were administered individually in a concentration of 100 nM. Tests were carried out in triplicates.

The compound CDR132L, an LNA-DNA mixmer having a phosphorothioate backbone, was identified as most potent compound from the anti-miR-132 structure analogue library.

The structure of CDR132L is as follows:

5'-dA*+T*dG*+G*dC*+T*dG*+T*dA*+
G*dA*dC*dT*dG*+T*+T-3' (SEQ ID NO: 3)

wherein dA is 2'deoxyadenosine, dG is 2'deoxyguanosine, dC is 2'deoxycytidine and T is thymidine, wherein +T is an LNA-T building block and +G is an LNA-G building block and wherein * is a phosphorothioate linkage.

EXAMPLE 2—TOXICOLOGY PROFILING 2.1 Study aim: Toxicity profiling of CDR132L 2.2 Study Outline:

An in vitro cytotoxicity assay was carried out in human liver cell cells (HepG2) and isolated neonatal cardiomyocytes (NRCM). A colorimetric commercial MTT assay was used to assess cytotoxicity. After addition of individual compounds, cells were incubated in DMEM medium for 48 h. The effect of CDR132L (red) was compared to a scrambled LNA oligonucleotide, used as control (blue) in a dose range of 0.01-100 µM. The therapeutic dose range is marked in grey.

Figure 1B:
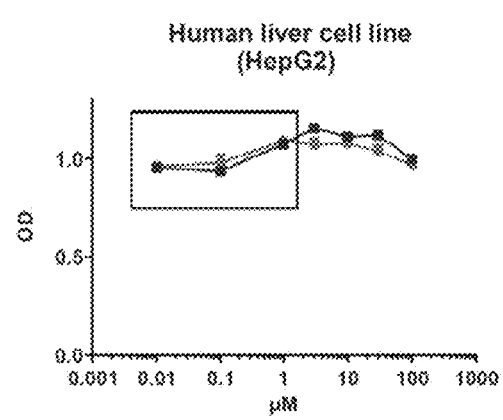
FIG. 1B: Effect of CDR132L compared to a scrambled LNA oligonucleotide, used as control in human liver cell cells (HepG2).

2.3 Results: No significant toxicity of CDR132L in HepG2 cells and NRCM was found over the therapeutic dose range (cf. FIGS. 1A and 1B).

EXAMPLE 3—LEFT VENTRICULAR REVERSE REMODELING OF THE FAILING HEART BY ADMINISTRATION OF CDR132L IN A TRANSGENIC MOUSE MODEL 3.1 Study aim: Test efficacy of CDR132L in reversing heart failure in a mouse model of heart failure.

3.2 Study Outline:

Model of cardiac hypertrophy: Transgenic (TG) mice with cardiac miR-132 overexpression (Ucar et al. 2012).

Figure 2A:
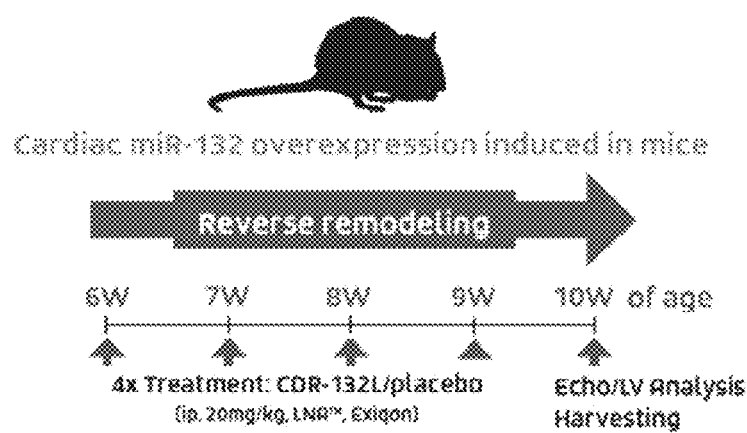
FIG. 2A: Experimental design for treatment of transgenic mice having cardiac miR-132 overexpression with CDR132L or placebo.

Treatment: weekly 20 mg/kg ip. CDR132L or placebo (cf. FIG. 2A)

Groups: wild type (WT) littermate +placebo, WT+CDR132L, TG+placebo, TG+CDR132L. n=6/group.

Figure 2B:
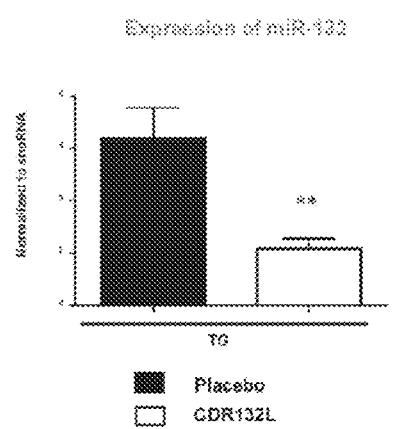
FIG. 2B: Expression levels of miR-132 after treatment with CDR132L or placebo in a transgenic mouse model.

Expression levels of miR-132 were detected via qPCR. Statistical test: unpaired t-test. (FIG. 2B).

**$p<0.01$, n=6/group.

Figure 3A:
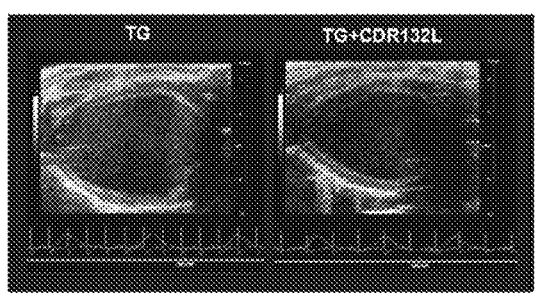
FIG. 3A: Echocardiography heart images of transgenic (TG) mice with or without CDR132L treatment.

3.3 Results:

Representative echocardiography images of the heart (FIG. 3A).

Figure 3B:
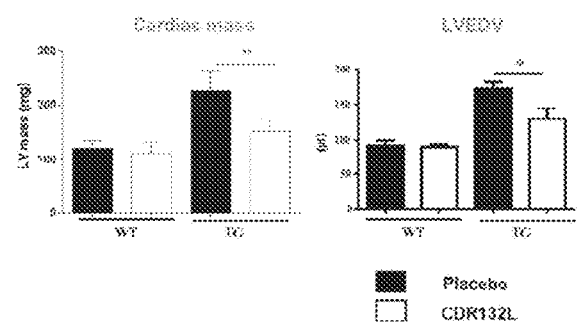
FIG. 3B: Cardiac hypertrophy as measured by cardiac mass and end-diastolic volume (LVEDV) in wildtype (WT) and transgenic (TG) mice with placebo or CDR132L treatment.

CDR132L reverses hypertrophy as measured by cardiac mass and enddiastolic volume (LVEDV) (FIG. 3B).

Figure 3C:
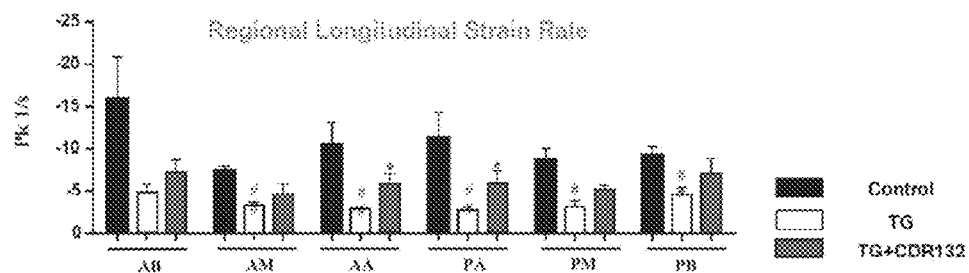
FIG. 3C: Regional longitudinal strain rate in segments of the left ventricle (AB, anterior basal; AM, mid anterior; AA, anterior apex; PA posterior apex; PM, mid posterior and PB, posterior basal) in control or transgenic (TG) mice with placebo or CDR132L treatment.

CDR132L improves regional contractile function in most segments of the left ventricle (AB, anterior basal; AM, mid anterior; AA, anterior apex; PA posterior apex; PM, mid posterior and PB, posterior basal) (FIG. 3C).

EXAMPLE 4—ADMINISTRATION OF CDR132L IN A MOUSE MODEL OF POST-MI HEART FAILURE 4.1 Study aim: Test efficacy of CDR132L in a mouse model of post-MI heart failure 4.2 Study Outline Mouse model of myocardial infarction (MI): permanent ligation of coronary artery (LAD) in C57BL/6N mice (Kolk et al., 2009).

Figure 4:
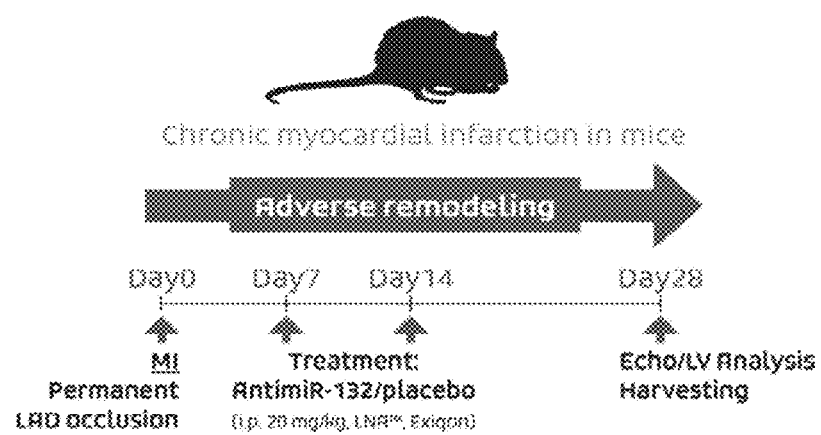
FIG. 4: Experimental design to test efficacy of CDR132L in a mouse model of post-MI heart failure.
Figure 5A:
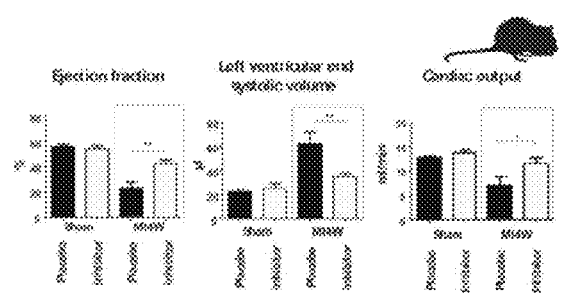
FIG. 5A: Effect of CDR132L (inhibitor) treatment on post-MI left ventricular dysfunction measured as ejection fraction, left ventricular end systolic volume and cardiac output.
Figure 5B:
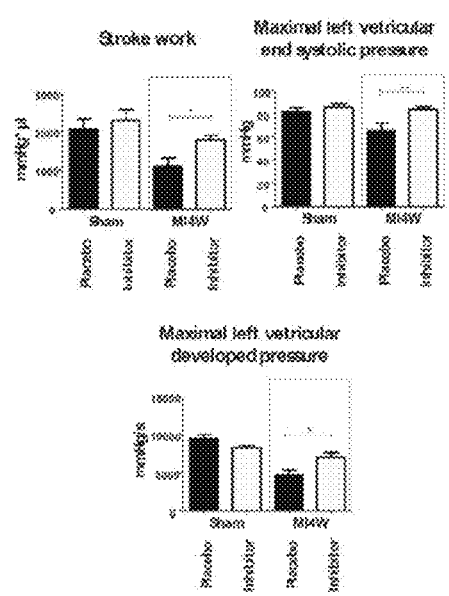
FIG. 5B: Effect of CDR132L (inhibitor) treatment on load independent parameters of systolic contractile function measured as stroke work, maximal left ventricular end systolic pressure and maximal left ventricular developed pressure.

Groups: MI or sham, treated with CDR132L or placebo
Treatment: 20 mg/kg ip, on day 7 and 14 post-MI
Endpoint: LV function at day 28 post-MI. n=6-7/group. (FIG. 4), 4.3 Results:

CDR132L treatment improves post-MI left ventricular dysfunction (FIG. 5A). Load independent parameters of systolic contractile function were also improved (FIG. 5B) (*$p<0.05$).

Figure 6:
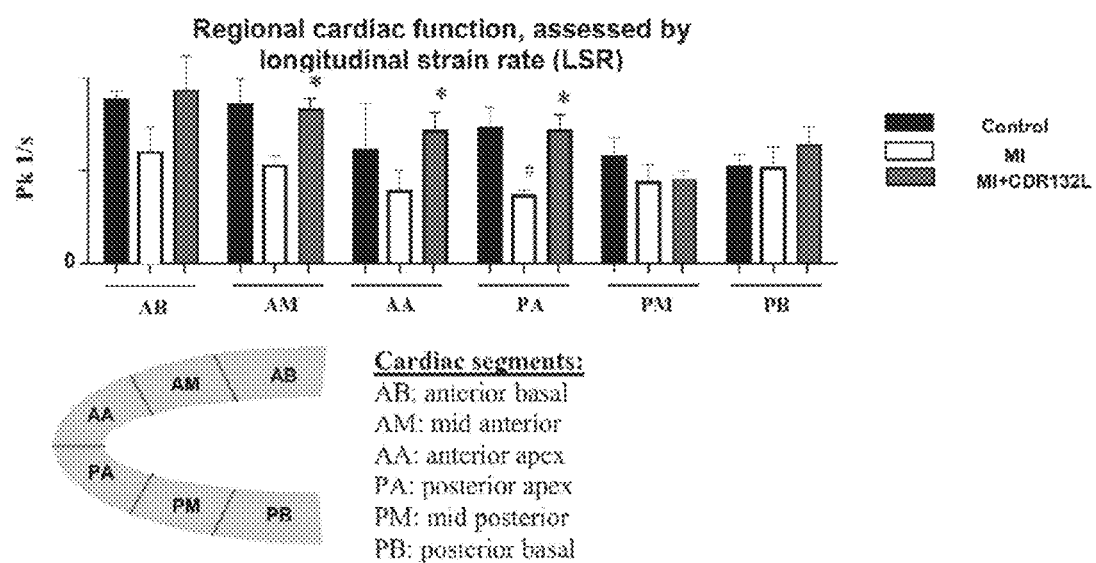
FIG. 6: Effect of CDR132L treatment on regional cardiac function, assessed by longitudinal strain rate in control and MI mice without or with CDR132L treatment.

CDR132L treatment also improves longitudinal strain rate (LSR) and thus reverses the post-MI contractile dysfunction in individual cardiac segments in the remote area of the heart. (*$p<0.05$) (FIG. 6).

Figure 7A:
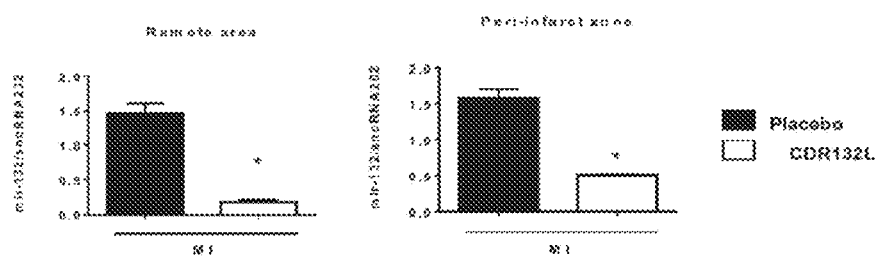
FIG. 7A: Expression of miR-132 in cardiac tissues shown in the remote (non-infarct) area and the peri-infarct zone with placebo or CDR132L treatment.

CDR123L treatment effectively silences miR-132 expression in cardiac tissues, in e.g. remote (non-infarct) area and peri-infarct zone (FIG. 7A).

Figure 7B:
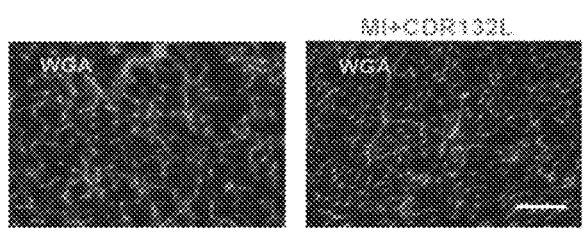
FIG. 7B: Cardiomyocyte size in the remote area of the post-MI heart without or with CDR132L treatment.

At histological level, CDR132L reduces cardiomyocyte size in remote area of the post-MI heart (FIG. 7B).

Figure 7C:
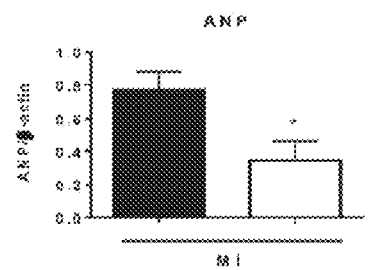
FIG. 7C: Expression of the cardiac stress signal ANP in the post-MI heart with placebo or CDR132L treatment.

At tissue level, CDR132L reduces the expression of the cardiac stress signal ANP in the post-MI heart (FIG. 7C).

EXAMPLE 5—TEST OF CDR132L IN A PIG MODEL OF POST-MI HEART FAILURE 5.1 Study aim: Proof of in vivo efficacy of CDR132L in a clinically relevant model of post-myocardial infarction.

5.2 Study Setup:

Pig model of myocardial infarction elicited by 90 min ischemia (LAD occlusion) and subsequent reperfusion.

Groups: Placebo or CDR132L, n=6 per group.

Figure 8:
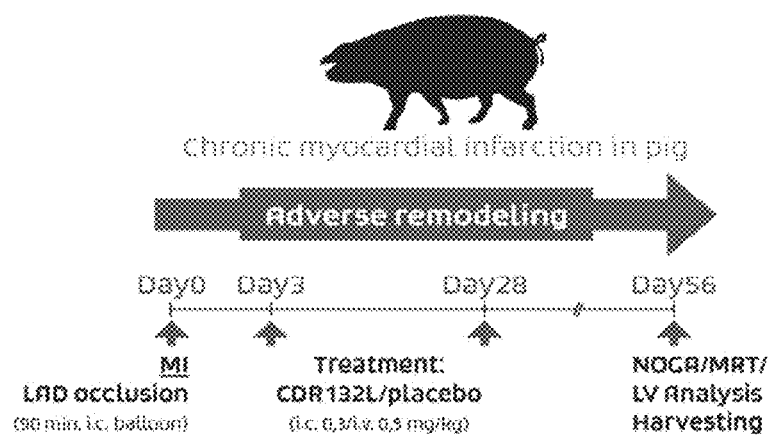
FIG. 8: Experimental design to test CDR132L in a pig model of post-MI heart failure.

Treatment: twice, on day 3 and day 28 post-MI, 0.3 mg/kg intracoronary and 0.5 mg/kg intravenously, respectively (FIG. 8).

Endpoint: 8 weeks post-MI. Primary outcome measures: EF and LV remodeling.

5.3 Results:

CDR132L treatment averts maladaptive remodeling and improves function, as determined by measurement of enddiastolic volume, endsystolic volume, ejection fraction and left ventricular function (FIGS. 9A-D).

Figure 9A:
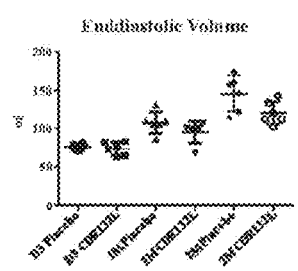
FIG. 9A: Effect of CDR132L treatment on the end-diastolic volume.
Figure 9B:
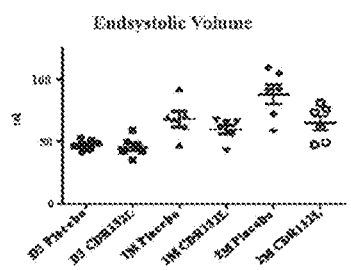
FIG. 9B: Effect of CDR132L treatment on the end-systolic volume.
Figure 9C:
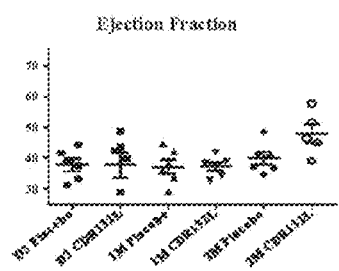
FIG. 9C: Effect of CDR132L treatment on the ejection fraction.
Figure 9D:
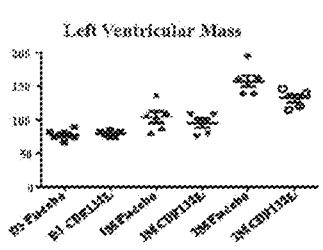
FIG. 9D: Effect of CDR132L treatment on the left ventricular function.
Figure 9E:
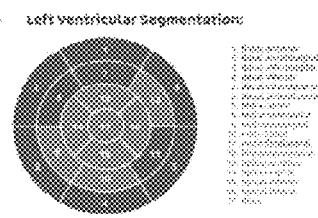
FIG. 9E: Effect of CDR132L treatment on segmental contractility in segments corresponding to surviving/remote myocardium.

CDR132L treatment improves segmental contractility in segments corresponding to surviving/remote myocardium; cardiac MRI at endpoint: n=6/group, red area: $p<0.05$ (FIG. 9E).

Figure 10:
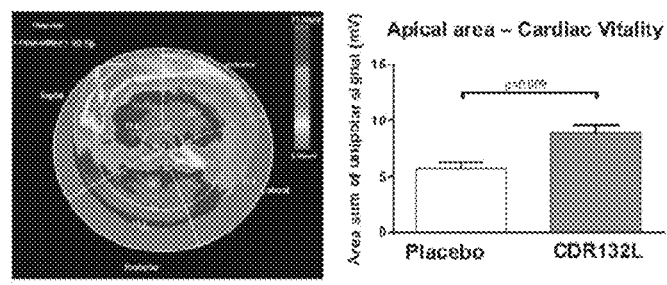
FIG. 10: Effect of CDR132L treatment on cardiac LV viability in the apical area.

CDR132L treatment averts maladaptive remodeling and improves LV viability in the apical area as determined by NOGA, electro-anatomical mapping at endpoint: n=6/group, placebo vs CDR132L: $p<0.05$ (FIG. 10).

Figure 11:
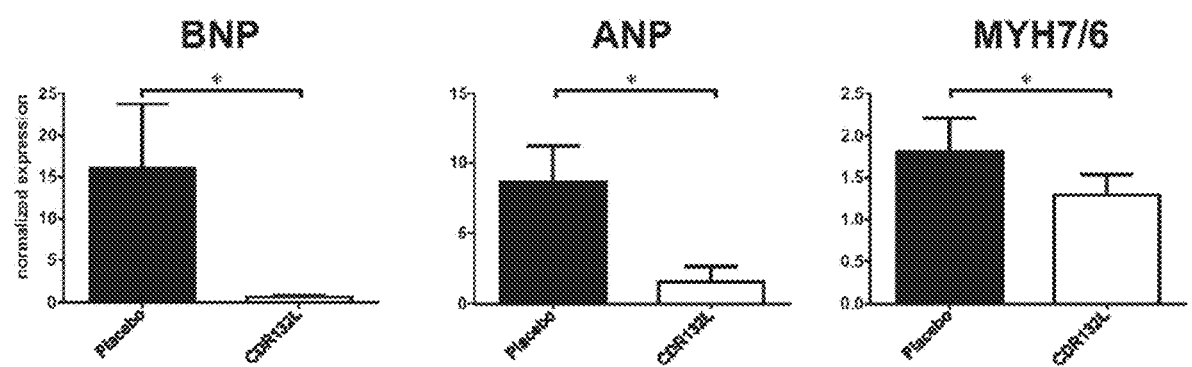
FIG. 11: Tissue expression of pathologic heart failure markers BNP, ANP and myosin heavy change isoforms MYH7/6 with placebo or CDR132L treatment.

CDR132L normalizes the tissue expression of pathologic heart failure markers in ANP and BNP and provides a shift in myosin heavy change isoforms, i.e. MYH7/6 ratio (FIG. 11).

Figure 12A:
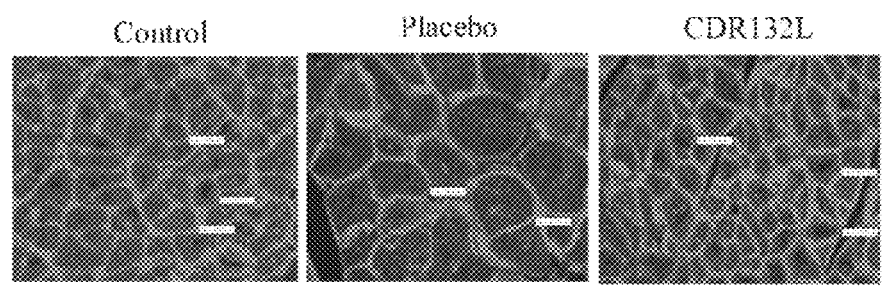
FIG. 12A: Cardiomyocyte hypertrophy in remote LV areas as assessed by photomicrography images with placebo or CDR132L treatment.
Figure 12B:
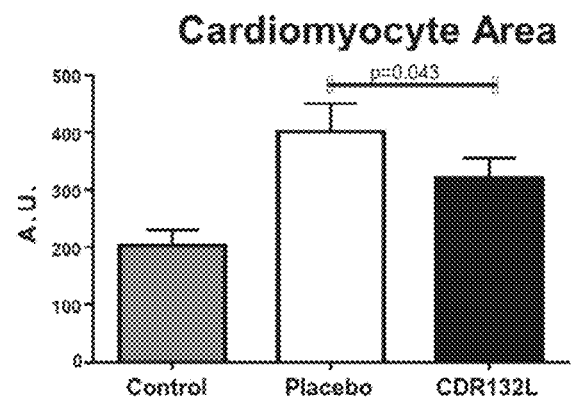
FIG. 12B: Cardiomyocyte area in remote LV areas with placebo or CDR132L treatment.

At histological level, CDR132L treatment effectively reduces cardiomyocyte hypertrophy in remote LV areas representative photomicrography images of LV area (WGA/DAPI Staining 20×) (FIG. 12A) and graphic depiction (FIG. 12B), n=6/group, placebo vs CDR132L: $p<0.05$.

EXAMPLE 6—PD PROFILE/TARGET ENGAGEMENT OF CDR132L IN PIGS 6.1 Study Set Up:

Treatment: 1×, day 0, 0.5 mg/kg or 5 mg/kg intracoronary perfusion, n=3 pigs/group, placebo vs CDR132L: $p<0.05$.

qPCR tissue miRNA assay at endpoint (24 h post-treatment).

Figure 13:
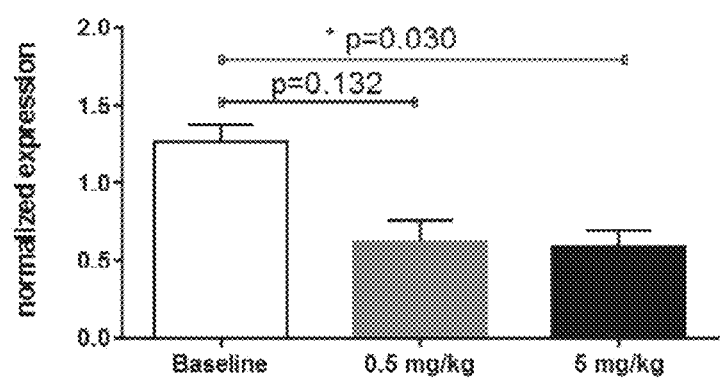
FIG. 13: Cardiac miR-132 levels after single dose of CDR132L treatment.

6.2 Results:

A single dose of CDR132L treatment dose-dependently silences cardiac miR-132 levels (FIG. 13).

Figure 14:
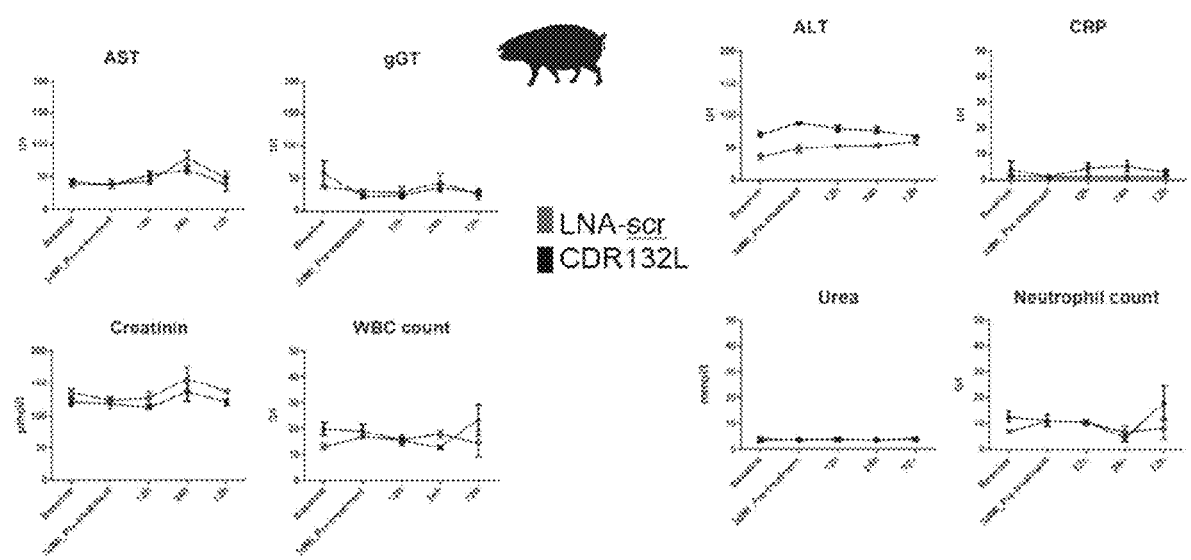
FIG. 14: Effect of CDR132L treatment on organ toxicity in pigs.

EXAMPLE 7—ORGAN TOXICOLOGY PROFILING 7.1 Study Set Up:
Treatment: twice, on day 3 and day 28 post-MI, 0.3 mg/kg intracoronary and 0.5 mg/kg intravenously, respectively.
Serial blood sampling, endpoint: 72 h-post treatment, n=6 pigs/group, placebo vs CDR132L: p<0.05.
7.2 Results:
CDR132L treatment in vivo does not elicit any organ toxicity in pigs (FIG. 14).

EXAMPLE 8—CARDIAC LEVELS OF FOXO3 AND SERCA2 MRNA IN A MOUSE MODEL OF HEART FAILURE

Figure 15:
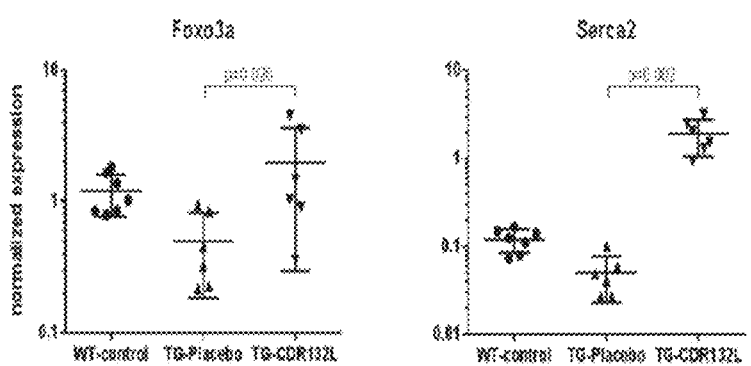
FIG. 15: Cardiac levels of FoxO3 and SERCA2 mRNA in wildtype (WT-control) and transgenic (TG) mice with placebo or CDR132L treatment.

Cardiac FoxO3 and Serca2 mRNA levels were measured in control and miR-132 TG mice treated with intraperitoneal injection of either control scrambled oligonucleotide or CDR132L, weekly, 4 times. All values represent mean±SEM. *P<0.05 (FIGS. 15A and 15B)

EXAMPLE 9—COMPARISON OF DIFFERENT OLIGONUCLEOTIDES

The purpose of this study was to evaluate therapeutic effect of the novel miR-132-3p inhibitor CDR132L according to the prevent invention with two comparative oligonucleotides. The two comparative oligonucleotides exhibit the same oligonucleotide sequence and a phosphorothioate backbone as CDR132L but differ in the distribution of LNA building blocks within the molecule. CDR2u1 harbors two LNA building blocks at the 5' and the 3' end, while for CDR301 each nucleotide carries an LNA building block.

To test the efficiency, the different oligonucleotides were administered to neonatal rat cardiomyocytes (NRCMs). Effects of this treatment were monitored by quantitative real-time PCR (qRT-PCR) following alterations in expression of miR-132-3p and its known target gene FoxO3 (Forkhead box 03).

The experimental design and the results are shown in FIG. 16: (A) Overview of the experimental setup. Neonatal rat cardiomyocytes were seeded on day 0 and treated with the oligonucleotides CDR132L, CDR2u1 or CDR301 (100 nM each) on day 1. At the endpoint, cells are harvested for gene expression analysis. (B) Expression levels of miR-132-3p after treatment with CDR132L, CDR2u1 or CDR301. (C) Expression levels of the miR-132-3p target gene Forkhead box O3 (FoxO3) after treatment with CDR132L, CDR2u1 or CDR301. Data are mean±SD. P values oligonucleotides versus placebo were determined by two-tailed Student's t test.

Figure 16A:
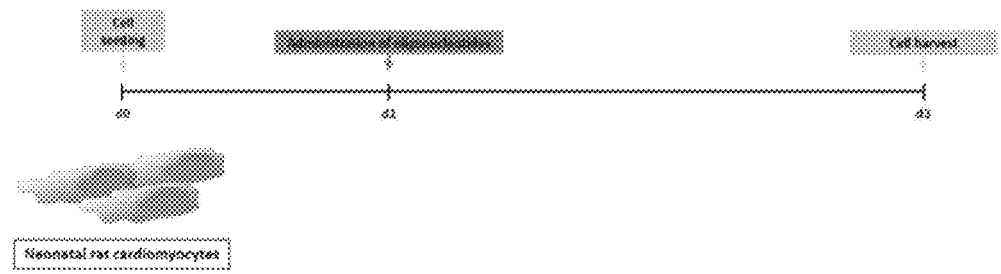
FIG. 16A: Overview of the experimental setup for the comparison of oligonucleotides.
Figure 16B:
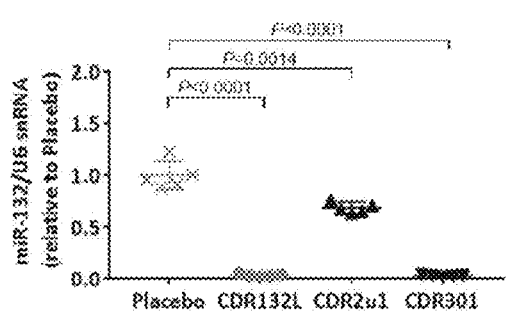
FIG. 16B: Expression levels of miR-132after treatment with oligonucleotides CDR132L, CDR2u1 or CDR301.
Figure 16C:
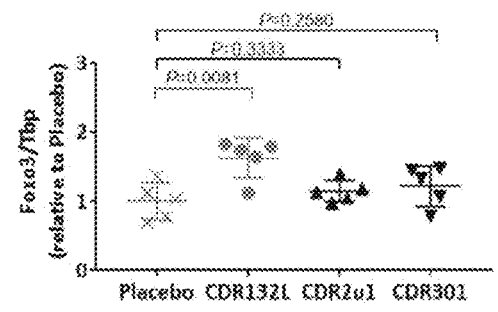
FIG. 16C: Expression levels of FoxO3 after treatment with oligonucleotides CDR132L, CDR2u1 or CDR301.

Treatment of NRCMs with CDR132L and CDR301 led to a significant reduction of miR-132-3p levels by 96%, while CDR2u1 reduced the miRNA expression by 30% (FIG. 16A-B). Further, treatment with CDR132L led to a significant depression of the miR-132-3p target gene Foxo3, which was not achieved with CDR2u1 and CDR301 (FIG. 16C).

In summary, our data demonstrate a superior inhibitory effect of CDR132L compared to CDR2u1 and CDR301 indicated by significantly lowered expression levels or miR-132-3p and significant repression of its target gene FoxO3.

EXAMPLE 10—EFFECTS OF CDR132L In Cardiac Fibrosis

The purpose of this study was to evaluate antifibrotic therapeutic effects of CDR132L in an in vivo model of fibrosis.

Figure 17:
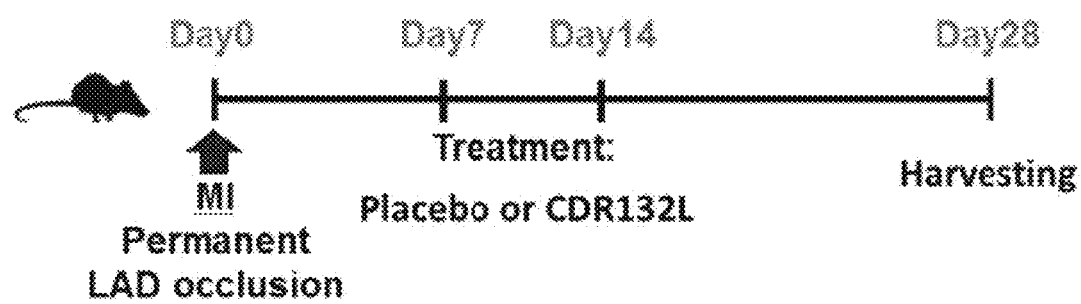
FIG. 17: Experimental design to evaluate antifibrotic therapeutic effects of CDR132L in an in vivo model of fibrosis.

For in vivo proof of antifibrotic activity, the mouse model of myocardial infarction (MI) by permanent left anterior descending coronary artery (LAD) ligation in C57BL/6N mice was used. CDR132L treatment was applied at day 7 and 14 placebo (scrambled oligo analogue to CDR132L, 20 mg/kg) and CDR132L (20 mg/kg). Groups included the control operated group (sham operated mice) and LAD-ligated mice (MI, myocardial infarction), receiving either placebo or CDR132L: Sham+placebo, Sham+CDR132L, MI+placebo, MI+CDR132L. n=6-7/group. The experimental design is described in FIG. 17.

The assessment of the antifibrotic effect of CDR132L in vivo in post MI heart failure is shown in FIG. 18. Fibrosis (shown as % of collagen deposition detected by Picro-sirius red (PSR) staining and Collagen Type III Alpha 1 Chain (Col3a1) gene expression relative to β-Actin) was attenuated after MI by treatment with CDR132L. Groups included the control operation group (sham operated mice) and LAD ligated mice (MI), receiving either placebo (black column) or CDR132L (white column): Sham+placebo, Sham+CDR132L, MI+placebo, MI+CDR132L. Statistical test (unpaired t-test) was done between MI mice treated with placebo or CDR132L. **p<0.01, n=6-7/group.

Figure 18A:
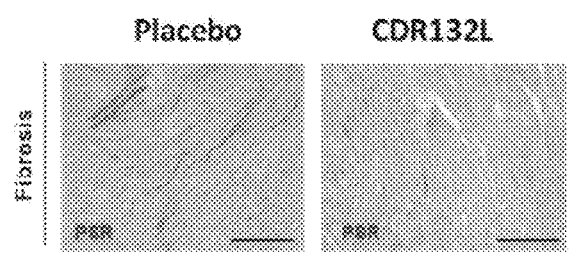
FIG. 18A: Histological effect of CDR132L treatment on fibrosis shown as collagen deposition.
Figure 18B:
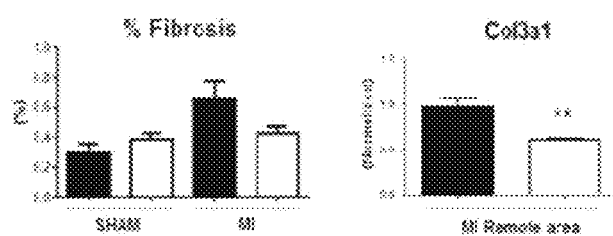
FIG. 18B: Effect of CDR132L treatment on gene expression for the fibrosis marker Collagen Type III Alpha 1 Chain (Col3a1).

According to the histological results, fibrosis was attenuated after CDR132L treatment (FIG. 18A). This was confirmed at molecular level, with reduced gene expression for fibrosis markers like Collagen Type III Alpha 1 Chain (Col3a1) (FIG. 18B).

EXAMPLE 11—EFFECTS OF CDR132L IN PULMONARY AND HEPATIC FIBROSIS

The antifibrotic effect of CDR132L was tested in in vitro models for pulmonary and hepatic fibrosis. For that, human primary fibroblasts derived from liver (human primary liver fibroblasts, HPLF, PeloBiotech) and lung (normal human primary lung fibroblasts, NHLF, Lonza) were stimulated with pro-fibrotic agents and treated with CDR132L. Therapeutic effects of CDRL132L were monitored by following key processes within the fibrotic pathway including proliferation rate and alterations in expression of fibrotic marker genes at endpoint. In addition, expression of miR-132-3p was assessed to prove effective CDR132L treatment.

To determine cell proliferation, a Cell Proliferation ELISA (Enzyme-linked Immunosorbent Assay) Kit (provided by Roche) was used. This colorimetric assay allows to quantitate cell proliferation based on the measurement of BrdU (Bromdesoxyuridin) incorporated in newly synthesized DNA of proliferating cells. The amount of incorporated BrdU has been detected and quantified. Absorbance values directly correlate to the amount of DNA synthesis and hereby to the number of proliferating cells in the respective microcultures. Gene expression has been assessed using quantitative real-time PCR (qRT-PCR) measuring expression levels of miR-132-3p and fibrotic markers including Collagen 1A1 (COL1A1), Collagen 1A2 (COL1A2), and Matrix Metallopeptidase 2 (MMP2).

FIG. 19 refers to the in vitro model of liver fibrosis: (A) Overview of the experimental setup. Human primary liver fibroblasts (provided by PeloBiotech) were seeded on day 0 and treated with fibrotic stimulus (10 ng/ml TGF-β in normal growth medium (complete fibroblast medium supplemented with 10% FBS)) and CDR132L (100 nM) on day 1. At endpoint, cell proliferation and gene expression of fibrotic markers have been assessed. (B) Expression levels of miR-132-3p after treatment with CDR132L. (C) Proliferation assessed by monitoring of BrdU (Bromdesoxyuridin) incorporation during DNA synthesis. The BrdU reagent has been added to the medium 20 h before endpoint. (D) Expression levels of fibrotic marker genes (Collagen 1A1 (COL1A1), Collagen 1A2 (COL1A2), and Matrix Metallopeptidase 2 (MMP2)). In (B) and (D) dashed line indicates expression level of unstimulated control cells. Data are mean±SD. P values CDR132L versus control were determined by two-tailed Student's t test.

Figure 19A:
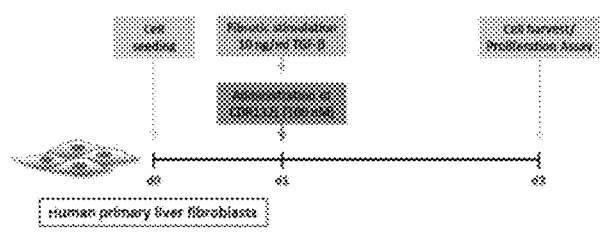
FIG. 19A: Experimental design to test the effects of CDR132L in liver fibrosis.
Figure 19B:
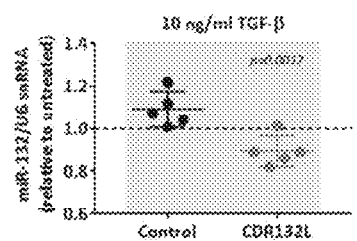
FIG. 19B: Expression of miR-132 in stimulated liver fibroblasts without or with CDR132L treatment.
Figure 19C:
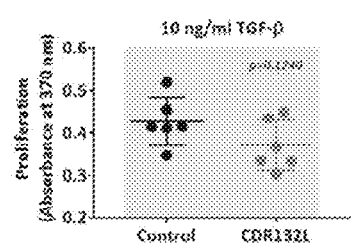
FIG. 19C: Proliferation of stimulated liver fibroblasts without or with CDR132L treatment.
Figure 19D:
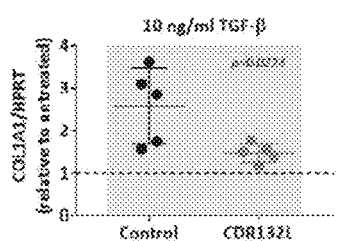
FIG. 19D: Expression of fibrotic marker genes COL1A1, COL1A2 and MMP2 in stimulated liver fibroblasts without or with CDR132L treatment.
Figure 19D:
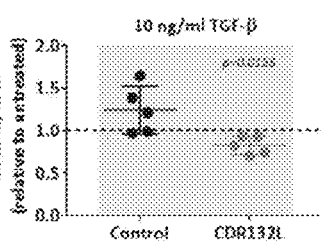
Figure 19D:
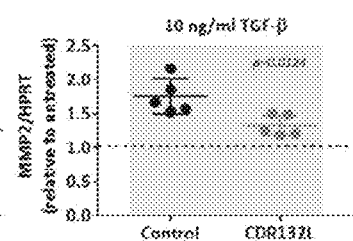

Stimulation of HPLFs with transforming growth factor beta (TGF-β) (FIG. 19A) led to slight induction of miR-132-3p that was significantly reduced by CDR132L treatment (FIG. 19B). Further, this compound reduced fibroblast proliferation (FIG. 19C) and fibrotic gene expression including COL1A1, COL1A2, and MMP2 (FIG. 19D).

Figure 20A:
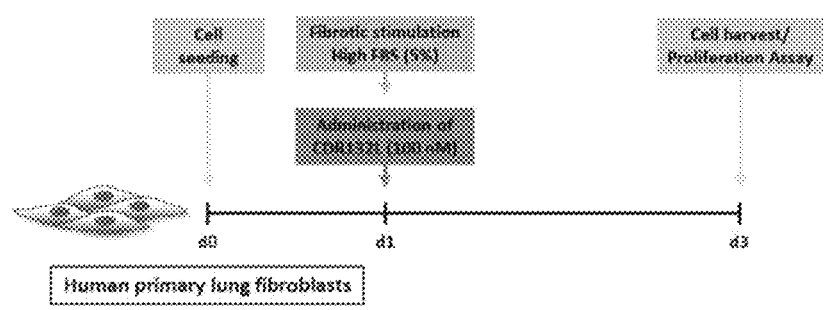
FIG. 20A: Experimental design to test the effects of CDR132L in lung fibrosis.

FIG. 20 refers to the in vitro model of lung fibrosis: (A) Overview of the experimental setup. Normal human lung fibroblasts (provided by Lonza) were seeded on day 0 and treated with fibrotic stimulus (High FBS (5%) in fibroblast growth medium and CDR132L (100 nM) on day 1. At endpoint, cell proliferation and gene expression have been assessed. (B) Expression levels of miR-132-3p after treatment with CDR132L. (C) Proliferation assessed by monitoring of BrdU (Bromdesoxyuridin) incorporation during DNA synthesis.

The BrdU reagent has been added to the medium 20 h before endpoint. In (B) dashed line indicates expression level of unstimulated control cells. Data are mean±SD. P values CDR132L versus control were determined by two-tailed Student's t test.

Figure 20B:
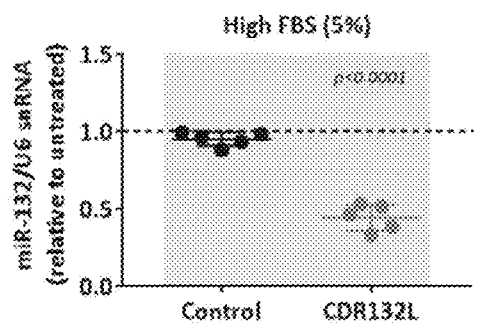
FIG. 20B: Expression of miR-132in stimulated lung fibroblasts without or with CDR132L treatment.
Figure 20C:
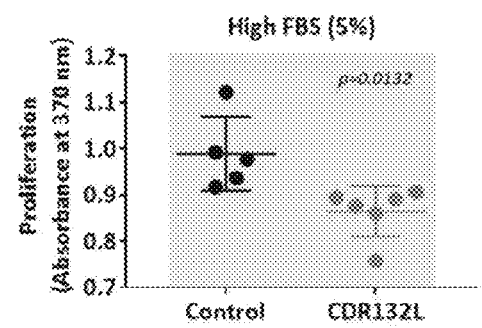
FIG. 20C: Proliferation of stimulated lung fibroblasts without or with CDR132L treatment.

In NHLF cells, after fibrotic stimulation with high FBS (5% compared to normal growth conditions of 2% FBS) (FIG. 20A) no elevation of miR-132-3p was observed (FIG. 20B). Nevertheless, treatment with CDR132L led to a significant reduction of the targeted microRNA (FIG. 20B) and fibroblast proliferation (FIG. 20C).

In summary, our data demonstrate a significant antifibrotic effect of the oligonucleotide analogue CDR132L in liver- or lung-derived fibroblasts as well as in cardiac tissue. We assume this effect may be based on the drug's antiproliferative capacity, and/or on its effect on the extracellular matrix protein expression.

REFERENCES

1. Barry, S. P.; Townsend, P. A. (2010). What causes a broken heart-Molecular insights into heart failure. Int Rev Cell Mol Biol 284, 113-179.
2. Datta, S. R.; Brunet, A.; Greenberg, M. E. (1999). Cellular survival: a play in three Akts. Genes Dev. 13, 2905-2927.
3. DeBosch, B. J.; Muslin, A. J. (2008). Insulin signaling pathways and cardiac growth. J Mol Cell Cardiol. 44, 855-864.
4. Frescas, D.; Valenti, L.; Accili, D. (2005). Nuclear trapping of the forkhead transcription factor FoxO1 via Sirt1-dependent deacetylation promotes expression of glucogenetic genes. J Biol Chem. 280, 20589-20595.
5. Glas, D. J. (2010). PI3 kinase regulation of skeletal muscle hypertrophy and atrophy. Curr Top Microbiol Immunol. 346, 267-278.
6. Gottlieb, R. A.; Gustafsson, A. B. (2011). Mitochondrial turnover in the heart. Biochim Biophys Acta. 1813, 1295-1301.
7. Kolk, M. V.; Meyberg, D.; DenseT.; Tang-Quam, K. R.; Robbins R. C.; Reichenspurner, H.; Schrepfer. S (2009), J. Vis Exp. 32, pii: 1438. doi: 103791/1438
8. McMullen, J. R.; Shioi, T.; Huang, W. Y.; Zhang, L.; Tarnayski, O.; Bisping, E.; Schinke, M.; Kong, S.; Sherwood, M. C.; Brown, J. et al. (2004). The insulin-like growth factor 1 receptor induces physiological heart growth via the phosphoinositide 3-kinase (p110alpha) pathway. J Biol Chem. 279, 4782-4793.
9. Ni, Y. G.; Berenji, K.; Wang, N.; Oh, M.; Sachan, N.; Dey, A.; Cheng, J.; Lu, G.; Morris, D. J.; Castrillon, D. H. et al. (2006). Foxo transcription factors blunt cardiac hypertrophy by inhibiting calcineurin signaling. Circulation. 114, 1159-1168.
10. Ronnebaum, S. M.; Patterson, C. (2010). The foxO family in cardiac function and dysfunction. Annu Rev Physiol. 72, 81-94.
11. Skurk, C.; Izumiya, Y.; Maatz, H.; Razeghi, P.; Shiojima, I.; Sandri, M.; Sato, K.; Zeng, L.; Schiekofer, S.; Pimentel, D. et al. (2005). The FOXO3a transcription factor regulates cardiac myocyte size downstream of AKT signaling. J Biol Chem. 280, 20814-23.
12. Ucar, A. et al. (2012), Nat. Commun. 3: 1078. doi: 10.1038/ncornms2009.

The invention claimed is:

1. An oligonucleotide comprising a sequence of formula II:

5'-A+TG+GC+TG+TA+GACTG+T+T-3'
(SEQ ID NO: 2)

wherein A, T, G and C are deoxyribonucleotide building blocks and
wherein +G and +T are bridged nucleotide building blocks.

2. The oligonucleotide of claim 1, wherein +G and +T are locked nucleotide (LNA) building blocks having a 2'-O—CH2-4' bridge.

3. The oligonucleotide of claim 1 having a length of 16 building blocks.

4. The oligonucleotide of claim 1 comprising at least one modified internucleosidic linkage, including at least one phosphorothioate or phosphorodiamidate internucleosidic linkage.

5. The oligonucleotide of claim 1, wherein all internucleosidic linkages are phosphorothioate linkages.

6. The oligonucleotide of claim 1 comprising the sequence of formula III:

5'-dA*+T*dG*+G*dC*+T*dG*+T*dA*+
G*dA*dC*dT*dG*+T*+T 3' (SEQ ID NO: 3)

wherein dA is 2'deoxyadenosine, dG is 2'deoxyguanosine, dC is 2'deoxycytidine and T is thymidine,
wherein +T is a locked nucleotide (LNA)-T building block and +G is a locked nucleotide (LNA)-G building block and
wherein * is a phosphorothioate linkage.

7. The oligonucleotide of claim 1 conjugated to a heterologous moiety.

8. A pharmaceutical composition comprising an oligonucleotide of claim 1 and a pharmaceutically acceptable carrier.

9. A method of prevention or treatment of a cardic disorder commprising administering to a patient in need thereof an effective amount of the oligonucleotide of claim 1.

10. The method of claim 9, wherein the cardiac disorder is associated with, accompanied by and/or caused by pathological expression of miR-132.

11. The method of claim 9, wherein the cardiac disorder is a cardiac hypertrophy-associated disorder.

12. The method of claim 9, wherein the cardiac disorder is contractile dysfunction, cardiac decompensation or heart failure.

13. The method of claim 9, wherein the patient in need is selected from:
(i) patients having an increased risk for developing heart failure,
(ii) patients suffering from (congestive) heart failure, including patients having an increased risk of heart failure progression;
(iii) post-myocardial infarction patients, and/or
(iv) patients with congenital heart diseases associated to cardiac hypertrophy, pulmonal vein stenosis, atrial or ventricular septum defects.

14. The method of claim 9, wherein the administering is a monotherapy or in combination with a further medicament, selected from angiotensin-modulating agents, β-blockers, diuretics, aldosterone antagonists, vasodilators, ionotrophic agents, or combinations thereof.

15. A method of prevention or treatment of a fibrotic disorder comprising administering to a patient in need thereof an effective amount of the oligonucleotide of claim 1.

16. The method of claim 15, wherein the fibrotic disorder is selected from cardiac fibrotic disorders, atrial fibrosis, endomyocardial fibrosis or fibrosis resulting from a previous myocardial infarction, pulmonary fibrotic disorders, pulmonary fibrosis caused by occupational or environmental factors, pulmonary fibrosis caused by radiation treatment and/or treatment with medicaments or idiopathic pulmonary fibrosis, or hepatic fibrotic disorders, alcoholic liver disease or non-alcoholic fatty liver disease (NAFLD).

17. The method of claim 15, wherein the adminstering is a monotherapy or in combination with a further medicament.

18. The method of claim 15, further comprising a step of determining the amount and/or activity of (i) miR-132 of (ii) at least one cardiac marker and/or (iii) at least one fibrotic marker in the patient to be treated before, during and/or after administration of the oligonucleotide.

19. A method of prevention or treatment of a cardiac disorder comprising administering to a patient in need thereof an effective amount of the pharmaceutical composition of claim 8 for use in medicine, including for use in human medicine.

20. The method of claim 19, wherein the cardiac disorder is selected from a disorder associated with, accompanied by and/or caused by pathological expression of miR-132.

21. The method of claim 19, wherein the cardiac disorder is a cardiac hypertrophy-associated disorder.

22. The method of claim 19, wherein the cardiac disorder is selected from contractile dysfunction, cardiac decompensation or heart failure.

23. The method of claim 19, wherein the patient is selected from:
   (i) patients having an increased risk for developing heart failure,
   (ii) patients suffering from (congestive) heart failure, including patients having an increased risk of heart failure progression;
   (iii) post-myocardial infarction patients, and/or
   (iv) patients with congenital heart diseases associated to cardiac hypertrophy, pulmonal vein stenosis, atrial or ventricular septum defects.

24. The method of claim 19, wherein the administration is a monotherapy or in combination with a further medicament, selected from angiotensin-modulating agents, β-blockers, diuretics, aldosterone antagonists, vasodilators, ionotrophic agents, or combinations thereof.

25. A method of prevention or treatment of a fibrotic disorder comprising administering to a patient in need thereof an effective amount of the pharmaceutical composition of claim 8.

26. The method of claim 25, wherein the fibrotic disorder is selected from cardiac fibrotic disorders, atrial fibrosis, endomyocardial fibrosis or fibrosis resulting from a previous myocardial infarction, pulmonary fibrotic disorders, particularly pulmonary fibrosis caused by occupational or environmental factors, pulmonary fibrosis caused by radiation treatment and/or treatment with medicaments or idiopathic pulmonary fibrosis, or hepatic fibrotic disorders, alcoholic liver disease or non-alcoholic fatty liver disease (NAFLD).

27. The method of claim 25, wherein the administering is a monotherapy or in combination with a further medicament.

28. The method of claim 25, further comprising a step of determining the amount and/or activity of (i) miR-132 of (ii) at least one cardiac marker and/or (iii) at least one fibrotic marker in the patient to be treated before, during and/or after administration of the pharmaceutical composition.

\* \* \* \* \*